United States Patent [19]

Brussee et al.

[11] Patent Number: 5,189,219

[45] Date of Patent: Feb. 23, 1993

[54] METHOD FOR THE PREPARATION OF ERYTHRO VICINAL AMINO-ALCOHOLS

[75] Inventors: Johannes Brussee; Arne van der Gen; Cornelis G. Kruse, all of Weesp, Netherlands

[73] Assignee: Duphar International Research B.V., Weesp, Netherlands

[21] Appl. No.: 810,139

[22] Filed: Dec. 19, 1991

[30] Foreign Application Priority Data

Dec. 24, 1990 [EP] European Pat. Off. ........ 90203498.2

[51] Int. Cl.$^5$ ........................................... C07C 209/52
[52] U.S. Cl. ................................... 564/356; 564/276; 564/357; 564/363
[58] Field of Search ................ 564/356, 357, 363, 276

[56] References Cited

FOREIGN PATENT DOCUMENTS 0170517 2/1986 European Pat. Off. .

OTHER PUBLICATIONS

Tetrahedron Letters, vol. 31, No. 10, 1990, pp. 1447–1450; W. R. Jackson et al: "Stereoselective Syntheses of Ephedrine . . . ".

Synthesis, No. 4, Apr. 1986, pp. 301–303; L. R. Krepski et al, "A New Synthesis of 2-Aminoalcohols from O--Trimethylsilyl . . . ".

Tetrahedron Synthesis, vol. 1, No. 3, Mar. 1990, pp. 163–166 Brussee et al: "Magnesium Ion Mediated Stereospecific . . . ".

Primary Examiner—Richard L. Raymond
Attorney, Agent, or Firm—Stevens, Davis, Miller & Mosher

[57] ABSTRACT

The present invention is concerned with the preparation of erythro N-substituted vicinal aminoalcohol derivatives from hydroxyl-protected cyanohydrin derivatives by successive Grignard reaction, transimination using a primary amine, reduction of the resulting imine and removal of the hydroxyl-protecting group. The products are obtained either as a racemate or in an optically pure form, depending upon the stereochemical composition of the cyanohydrin derivatives.

3 Claims, No Drawings

METHOD FOR THE PREPARATION OF ERYTHRO VICINAL AMINO-ALCOHOLS

The present invention is concerned with a method for the preparation of erythro N-substituted vicinal amino-alcohol derivatives, and with the preparation of intermediates for use in this method.

Vicinal amino-alcohol derivatives can be prepared according to Krepski et al. (Synthesis 1986, 301) by reacting racemic silyl-protected cyanohydrins with Grignard reagent, followed by a reduction step and a deprotection step. In general, poor stereoselectivity in the reduction step was observed, resulting in erythro/threo mixtures of 1/1 to 24/1.

Optically pure hydroxy-protected cyanohydrins can be converted into the corresponding vicinal amino-alcohol compounds using a similar procedure. Again, the method results in a rather poor chiral induction (erythro/threo ratios of 15/1 up to 24/1). As a result, N-substituted compounds prepared from these vicinal amino-alcohol compounds can not be obtained directly in a stereochemically pure form.

Furthermore, Brussee et al. (Tetrahedron Asymmetry 1, 163; 1990) describe the synthesis of some optically pure N-substituted vicinal amino-alcohol derivatives according to a lengthy procedure, by first preparing a protected alpha-hydroxyketone (acyloin) by Grignard reaction of the corresponding hydroxyl-protected cyanohydrin and subsequent hydrolysis of the Grignard-reacted product, whereafter the resulting acyloin was isolated from the reaction product. This hydroxyl-protected acyloin was reacted in the second step with a primary amine to obtain an intermediate secondary imine, which was finally reduced to the desired N-substituted hydroxyl-protected vicinal amino-alcohol. By the introduction of magnesium ions and reduction at a low temperature (below 0° C.) very high diastereoselectivity was achieved (erythro/threo ratios above 100/1).

According to the present invention an erythro N-substituted vicinal amino-alcohol derivative of formula 1

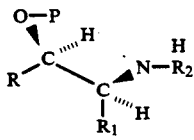  (1)

wherein
P is a group protecting the hydroxyl group;
R is a monocyclic or bicyclic aryl or heteroaryl group substituted with one or more groups X, wherein X is a hydroxy alkoxy(1-5C), alkyl(1-5C)carbonyloxy, amino, alkyl(1-5C)carbonylamino, alkyl(1-5C)sulphonylamino, nitro, alkyl(1-5C)sulphonyl, alkyl(1-5C)carbonyl, halogen, cyano, alkyl(1-5C), cycloalkyl(5-12C), or a cyclic group annelated with the aryl group or heteroaryl group, or wherein R is a saturated or unsaturated straight or branched alkyl group having 1-30 C-atoms which may be substituted with halogen, alkoxy(1-5C), alkylthio(1-5C), phenyl or phenoxy optionally $R_1$ and $R_2$ independently of each other are alkyl, alkenyl (2-8C), or phenyl or aralkyl(7-10C), optionally substituted with a group X is prepared without isolation of intermediate products by reacting a hydroxyl-protected cyanohydrin derivative of formula 2

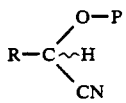  (2)

with a Grignard reagent of formula 3

$$R_1\text{—Mg—Hal} \quad (3)$$

yielding a Grignard reacted compound, followed by a novel transimination reaction using a primary amine of formula 4

$$R_2\text{—NH}_2 \quad (4)$$

and reduction of the resulting N-substituted imine, wherein P, R, $R_1$ and $R_2$ have the abovementioned meanings and Hal is a halogen atom.

The method according to the present invention avoids the lengthy procedures from the prior art, and enables the stereoselective preparation of hydroxyl-protected N-substituted vicinal amino-alcohol derivatives in a one-pot reaction starting from the corresponding hydroxyl-protected cyanohydrins, without the need for isolation of an intermediate product.

Surprisingly it was found that the process according to the present invention gave a high yield with unexpectedly high stereochemical induction at ambient temperature.

According to the present invention pure erythro compounds can be obtained, starting from racemic cyanohydrins. Furthermore, starting from optically pure cyanohydrins, the pure erythro compounds are optically pure too. This implies that during the latter reaction no racemisation of the cyanohydrin carbon atom occurs.

The final step in this preparation involves reduction of a compound of formula 5

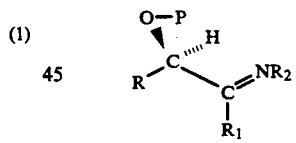  (5)

wherein P, R, $R_1$ and $R_2$ have the aforementioned meanings. This reduction can be established by the usual reagents employed for the conversion of imines into secondary amines, as described by Harada in "The Chemistry of the Carbon-Nitrogen Double Bond". pp. 276-293. Useful examples are (earth)alkali metal aluminumhydrides and borohydrides, (earth)alkali metals in protic solvents, and hydrogen gas in the presence of a metal catalyst. Advantageously use is made of reagents of the general structure $M_1M_2(A)_nH_{4-n}$, wherein $M_1$ is a metal from the group IA or IIA of the periodic system of elements, $M_2$ is boron or alumina, n is an integer having the value 0-3, and A is an electron-withdrawing substituent, e.g. of the type CN, halogen, alkoxy or dialkylamino. In particular, use can be made of a reagent wherein $M_2$ is boron, n is 0 or 1 and A is CN.

The intermediate according to formula 5 is prepared by protonation of the Grignard reacted compound of formula 6

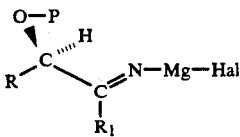

and the subsequent transimination of the resulting imine with a primary amine of formula 4 wherein P, R, $R_1$, $R_2$ and Hal have the aforementioned meanings. The above reaction is novel, and the important advantage of this transformation is that it is irreversible, resulting in a complete conversion of N-unsubstituted imine into the N-substituted derivative.

Suitable hydroxyl-protecting groups P are for example silyl groups of the general formula 7

wherein $R_3$ to $R_5$ independently of each other can be alkyl or alkenyl groups having 1-8 carbon atoms, phenyl or aralkyl having 1-10 carbon atoms, a tertiary alkyl group having 4-12 carbon atoms, an alkoxyalkyl group having 2-12 carbon atoms or the corresponding groups wherein oxygen is substituted by sulphur, or for example a dihydropyran-2-yl group, a tetrahydropyran-2-yl group, a dihydrofur-2-yl group or a tetrahydrofur-2-yl group, which groups may be substituted with an alkyl group having 1-6 carbon atoms, or the corresponding groups wherein oxygen is replaced by sulphur.

The compounds of formula 1 can be converted into the corresponding unprotected N-substituted ethanolamines by removal of the protecting group P. This protecting group can be removed by methods known in the art.

The resulting N-substituted ethanolamines, either as racemates, or as pure enantiomers are for example useful as pharmaceutically active agents. Examples of these are ephedrine, isoxsuprine, ritodrine, dilevalol, labetolol, sotalol, salbutamol and clenbuterol.

EXAMPLE 1

(1R,2S)-(−)-2-(Methylamino)-1-phenyl-1-[(tert.butyl-dimethyl-silyl)oxy]-propane.

To a magnetically stirred solution of 72 mmol of $CH_3MgI$ in 125 ml of ether was added dropwise 12 g (48mmol) of (R)-(+)-[tert-butyldimethylsilyl)oxy]-benzeneacetonitrile in 100 ml of anhydrous ether. After 4 hours reflux the excess of Grignard reagent was destroyed and the free imine was liberated by adding 50 ml of dry methanol. This was directly followed by a transimination reaction comprising the addition of a solution of 96 mmol of methylamine in 50 ml of methanol. After stirring for 30 min at room temperature the reaction mixture was cooled to 4° C. and 3.6 g (94 mmol) of $NaBH_4$ was added in three portions. The reaction mixture was stirred overnight at room temperature. Water was added and the mixture was extracted with ether (3×150 ml). The combined organic layers were washed twice with brine, dried on $K_2CO_3$ and evaporated.

Yield: 12.4 g (92.5%). NMR: 97% erythro, 3% threo.

Crystallization from absolute ethanol of this product as HCl salt afforded the pure captioned product. Analytical data were in complete agreement with the literature.

EXAMPLE 2

(1R,2S)-(−)-2-(Methylamino)-1-phenyl-1-propanol,HCl (Ephedrine.HCl).

Deprotection of the compound prepared according to Example 1 (12.3 g) was performed with $LiAlH_4$ in THF. The crude product (8.1 g contaminated with TBSOH) was dissolved in 100 ml of anhydrous ether and cooled in an ice bath. Dry HCl gas was passed until the amine was neutralized. The precipitate was filtered off, washed with anhydrous ether and dried.

Yield: 7.4 g (83%) ephedrine.HCl. Analytical data were identical to those of an authentic sample.

EXAMPLE 3

(1R,2S)-(−)-2-(Benzylamino)-1-phenyl-1-(tert.butyl-dimethyl-silyl)oxy]-propane.

The captioned compound was prepared in the same manner as described in Example 1, using benzylamine in the transimination reaction.

Yield: 94%. NMR: 98% erythro, 2% threo.

Crystallization from absolute ethanol as HCl salt afforded the pure captioned product. Analytical data were in complete agreement with literature.

EXAMPLE 4

(1R,2S)-(−)-2-(Benzylamino)-1-phenyl-1-propanol, HCl.

Prepared as described in Example 2 starting from the product obtained according to Example 3.

Yield: 89%.

$^1H$ NMR (220 MHz, MeOD, ppm): 7.2-7.6 (m, 10H, arom); 5.26 (d, 1H, J=3.1 Hz, HOCH); 4.37 (s, 2H, $CH_2C_6H_5$); 3.50 (m, 1H, $HCCH_3$); 1.10 (d, 3H, J=6.7 Hz, $CH_3$).

$[\alpha]_D=11.5°$ (c=1, MeOH), mp: 194°-195° C. Analytical data identical to those of a sample prepared by a method described in the literature.

EXAMPLE 5

(1R,2S)-(−)-2-(2-Phenylethylamino)-1-phenyl-1-[(tert.butyl-dimethylsilyl)oxy]-propane.

The captioned compound was prepared in the same manner as described in Example 1, using phenylethylamine in the transimination reaction.

Yield: 98%. NMR: 98% erythro, 2% threo.

Crystallization from absolute ethanol as HCl salt afforded the pure captioned compound. Analytical data were in complete agreement with those reported in the literature.

EXAMPLE 6

(1R,2S)-(−)-2-(2-Phenylethylamino)-1-phenyl-1-propanol,HCl.

Prepared as described in Example 2 starting from the product obtained according to Example 5.

Yield: 87%.

$^1H$ NMR (220 MHz, MeOD, ppm): 7.2-7.6 (m, 10H, arom); 5.21 (d, 1H, J=3.1 Hz, HOCH); 3.53 (m, 1H, $HCH_3$); 3.32 (m, 2H, $CH_2$); 3.09 (m, 2H, $CH_2$); 1.08 (d, 3H, J=6.7 Hz, $CH_3$). $[\alpha]_D=16.4°$ (c=1, MeOH), mp: 203°-205° C. Analytical data identical to those of a sample prepared from (1R,2S)-norephedrine and phenylacetaldehyde by a method described in the literature.

EXAMPLE 7

Ritodrine was synthesized according to the following scheme:

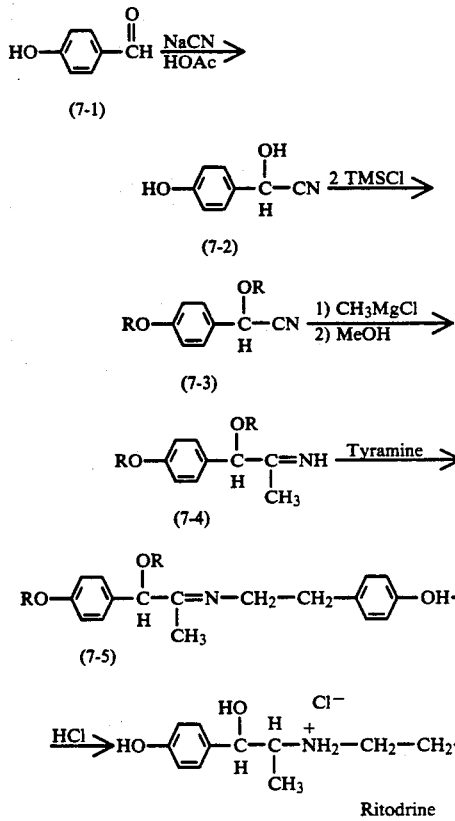

25 g of p-hydroxybenzaldehyde (compound 7-1) was dissolved in 55 ml of acetic acid en 38 ml of tetrahydrofuran (THF). Sodiumcyanide (43 g), dissolved in 70 ml of water, was added in 10 minutes while the temperature was kept at 20° C. After stirring for 4 hours, the reaction mixture was diluted with water en extracted with diethylether. The combined ether layers were washed with saturated NaCl solution, dried on $Na_2SO_4$ and evaporated at 35° C. The residu (32.8 g) contains compound 7-2

NMR(DMSO): 5.53(d,1H); 6.79(m.2H); 7.28(d,2H); 9.60(5,1H)

Trimethylsilyl chloride (12.4 g) was added to a solution of 9.4 g of imidazole in 85 ml of dry ethylacetate. After stirring for 15 minutes, 5.63 g p-hydroxymandelonitril was added. Stirring was continued overnight, and then the reaction mixture was washed thoroughly with water. The water layers were extracted with ethylacetate and the combined ethylacetate layers were dried on $Na_2SO_4$ and molecular sieves. Ethylacetate was evaporated to give 10.42 g of residu, that contained 8.1 g of compound 7-3

NMR (CDCl$_3$): 0.23(s,9H); 0.27(s,9H); 5.44 (s,1H); 6.88 (d,2H); 7.34(d,2H).

Conversion of compound 7-3 to ritodrine: To a solution of 8 ml of ether and 2 ml 3 mol/l CH$_3$MgI in ether was added 1 g of compound 7-3 in 7 ml of ether. The solution was stirred overnight and a white precipitate was formed. Then 8 ml of dry methanol was added, followed by addition of 0.7 g of tyramine (=4-(2-aminoethyl)phenol). Stirring was continued for 24 hours. Then 0.26 g of NaBH$_4$ was added in several portions and the reaction mixture was stirred for another 24 hours. The mixture was hydrolysed by adding 20 ml 4 N HCl. After 4 hours the solution is brought to pH=7 by addition of NaOH pellets. The solution contained ritodrine as monitored by HPLC; the ratio erythro/threo was about 7.5/1. Part of the solution was evaporated. The residu was treated with methanol and filtrated. The filtrate was evaporated and the residu was analyzed by NMR, demonstrating the presence of ritrodrine. HCl NMR (DMSO/CDCl$_3$5/1): 0.97 (d,3H); 2.92 (bt,2H); 3.31 (bm, 1H); 5.08 (bs,1H); 5.94 (bd,1H); 6.73 (d,2H); 6.76 (d,2H); 7.05 (d,2H); 7.16 (d,2H); 8.85 (bs,2H); 9.30 (s,1H); 9.35 (s,1H)

EXAMPLE 8

The ritodrine-derivative 8-6 was synthesized according to the following scheme:

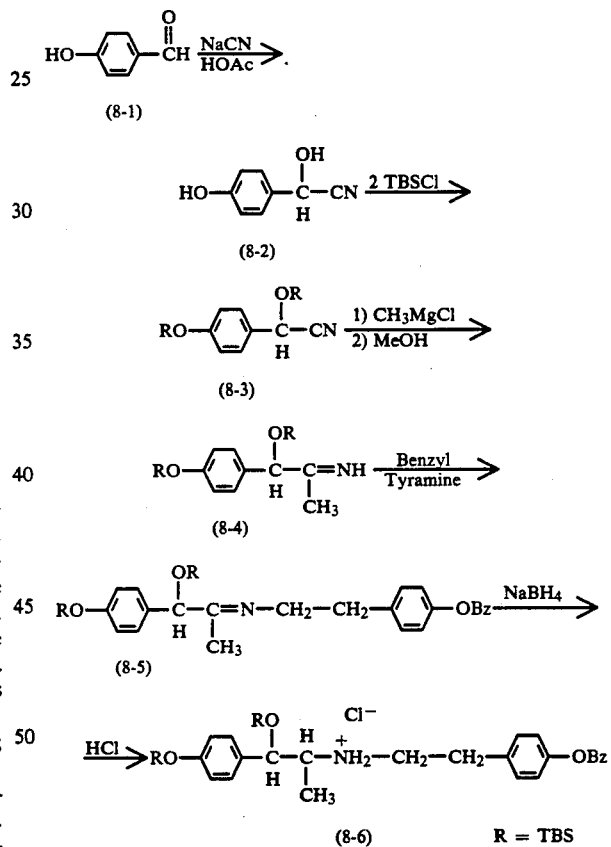

Compound 8-1 was transformed into compound 8-2 according to the corresponding reaction as described in Example 7. The cyanohydrine 8-2 was protected in the following way: 12.6 g of tert.butyldimethylsilylchloride was dissolved in 25 ml of ethylacetate and added to a solution of 6.3 g of imidazole in 80 ml of ethylacetate. After 15 minutes 5 g of p-hydroxy-mandelonitril (compound 8-2) in 25 ml of ethylacetate was added and stirring was continued for 22 hours. Water was added and the organic layer was washed three times with water. After drying on NazS0<and molecular sieves, ethylacetate was evaporated to give 11.3 g residu, containing 89% of compound 8-3 according to NMR.

NMR (CDCl$_3$): 0.11 (s,3H); 0.19 (s,3H); 0.20 (s,6H); 0.91 (s,9H); 0.98 (s,9H);
5.44 (s,1H); 6.85 (d,2H); 7.31 (d,2H).

Conversion of 8-3 into ritodrine-derivative 8-6.

To a solution of 15 ml of ether and 4 ml 3 mol/l of CH$_3$MgI in ether was added 2.7 g of compound 8-3 in 18 ml of ether. The solution was stirred for 22 hours. Under cooling, 20 ml of dry methanol was added, followed by 1.6 gram of benzyltyramine. The reaction mixture was stirred for 24 hours and then 0.54 g of NaBH$_4$ was added in small portions while cooling. After stirring for another 24 hours, 20 ml of 4N HCl was added while cooling. The reaction mixture was subsequently made alkaline (pH>9) by the addition of sodiumhydroxide solution. The precipitate was filtered off, the organic ether layer was washed neutral with water and dried. Evaporation of the solvent yielded 3.52 g of residu, containing the ritodrine-derivative 8-6 as a free base.

NMR (CDCl$_3$):−0.03 (s,3H); 0.09 (s,3H); 0.17 (s,6H); 0.84 (s,9H); 0.97 (s,9H); 1.03 (d,3H); 2.55-2.77(m,2H+1H); 2.86 (m,2H); 4.48 (d,1H); 5.02 (s,2H); 6.76 (d,2H); 6.86 (d,2H); 7.02 (d,2H); 7.11 (d,2H); 7.30-7.46 (m,5H).

We claim:

1. Method for the preparation of an erythro N-substituted vicinal amino-alcohol derivative of formula 1

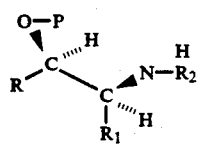

wherein
P is a group protecting the hydroxyl group;
R is a monocyclic or bicyclic aryl or heteroaryl group substituted with one or more groups X, wherein X is a hydroxy, alkoxy(1-5C), alkyl(1-5C)carbonyloxy, amino, alkyl(1-5C)carbonylamino, alkyl(1-5C)sulphonylamino, nitro, alkyl(1-5C)sulphonyl, alkyl(1-5C)carbonyl, halogen, cyano, alkyl(1-5C), cycloalkyl(5-12C), or a cyclic group annelated with the aryl group or heteroaryl group, or wherein R is a saturated or unsaturated straight or branched alkyl group having 1-30 C-atoms which may be substituted with halogen, alkoxy(1-5C), alkylthio(1-5C), phenyl or phenoxy optionally substituted with one or more groups X, and
R$_1$ and R$_2$ independently of each other are alkyl, alkenyl (2-8C), or phenyl or aralkyl(7-10C), optionally substituted with a group X by reacting a hydroxyl-protected cyanohydrin derivative of formula 2

with a Grignard reagent of formula 3

yielding a Grignard reacted compound, followed by a novel transimination reaction using a primary amine of formula 4

and reduction of the resulting N-substituted imine, wherein P, R, R$_1$ and R$_2$ have the abovementioned meanings and Hal is a halogen atom.

2. Method according to claim 1 wherein use is made of one of the enatiomers of the compound of formula 2 thereby yielding an optically pure erythro derivative of the compound according to formula 1.

3. Method for the preparation of a compound of formula 8

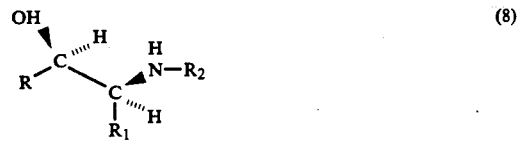

by using the method according to claim 1 or 2 and subsequently removing the hydroxyl-protecting group P of the compound of formula 1, wherein P, R, R$_1$, and R$_2$ have the abovementioned meanings.

* * * * *